US009999578B2

United States Patent
Foucault et al.

(10) Patent No.: US 9,999,578 B2
(45) Date of Patent: Jun. 19, 2018

(54) TRANSLUCENT AND SYRUPY COSMETIC COMPOSITION

(75) Inventors: Sophie Foucault, La Frette-sur-Seine (FR); Veronique Kowandy, Achicourt (FR); Veronique Trouillet, Saint-Pierre-les-Nemours (FR)

(73) Assignee: CHANEL PARFUMS BEAUTE, Neuilly-sur-Seine (FR)

( * ) Notice: Subject to any disclaimer, the term of this patent is extended or adjusted under 35 U.S.C. 154(b) by 0 days. days.

(21) Appl. No.: 14/126,651

(22) PCT Filed: Jun. 15, 2012

(86) PCT No.: PCT/IB2012/001335
§ 371 (c)(1),
(2), (4) Date: Dec. 16, 2013

(87) PCT Pub. No.: WO2012/172425
PCT Pub. Date: Dec. 20, 2012

(65) Prior Publication Data
US 2014/0120043 A1    May 1, 2014

Related U.S. Application Data

(60) Provisional application No. 61/497,611, filed on Jun. 16, 2011.

(51) Int. Cl.
| | |
|---|---|
| *A61K 8/06* | (2006.01) |
| *A61K 8/34* | (2006.01) |
| *A61K 8/37* | (2006.01) |
| *A61K 8/60* | (2006.01) |
| *A61Q 19/08* | (2006.01) |
| *A61K 8/97* | (2017.01) |

(52) U.S. Cl.
CPC .............. *A61K 8/062* (2013.01); *A61K 8/345* (2013.01); *A61K 8/37* (2013.01); *A61K 8/60* (2013.01); *A61K 8/602* (2013.01); *A61K 8/97* (2013.01); *A61Q 19/08* (2013.01); *A61K 2800/262* (2013.01)

(58) Field of Classification Search
None
See application file for complete search history.

(56) References Cited

U.S. PATENT DOCUMENTS

| | | | |
|---|---|---|---|
| 6,379,682 B1 * | 4/2002 | Tchinnis | A61K 8/06 424/401 |
| 6,689,371 B1 * | 2/2004 | Simonnet | A61K 8/06 424/401 |
| 7,488,471 B2 | 2/2009 | Mercier et al. | |
| 2003/0095990 A1 * | 5/2003 | Hua | A61K 8/068 424/400 |
| 2004/0081633 A1 * | 4/2004 | Mercier | A61K 8/062 424/70.12 |
| 2005/0100569 A1 | 5/2005 | Mercier et al. | |
| 2007/0071710 A1 * | 3/2007 | Maestro et al. | 424/74 |
| 2010/0210498 A1 * | 8/2010 | Poletti | 510/136 |
| 2010/0215598 A1 | 8/2010 | Poletti | |

FOREIGN PATENT DOCUMENTS

| | | | |
|---|---|---|---|
| EP | 2 218 440 | 2/2010 | |
| EP | 2 218 439 | 8/2010 | |
| FR | 2 846 234 | 10/2003 | |
| FR | 03 12595 | 10/2003 | |
| JP | 05-229916 | 9/1993 | |
| WO | 2006134282 | 12/2006 | |
| WO | 2009010356 | 1/2009 | |
| WO | WO2011015759 | * 2/2011 | ............... A61K 8/06 |

OTHER PUBLICATIONS

Rani et al. Viscosity of Liquid, Springer, 2007, p. 1, p. 6, 7, 86, 138-139.*
Gadhave, Determination of hydrophilic-lipophilic balance value, Int. J. Sci. Res., 2014, pp. 2319-7064.*
Megahed, Preparation of sucrose fatty acid esters as food emulsifiers and evaluation of their surface active and emulsification properties, 1999, vol. 50, Fasc. p. 280-282.*
Sisterna (Technical Note, Sisterna® sucrose esters in oil-in-water emulsions, 1999, pp. 1-6).*
International Search Report dated Nov. 15, 2012 in corresponding PCT application.

* cited by examiner

*Primary Examiner* — Bethany P Barham
*Assistant Examiner* — Ping Cao
(74) *Attorney, Agent, or Firm* — Young & Thompson

(57) ABSTRACT

Disclosed is a stable cosmetic composition having a syrupy texture while not being sticky, and translucent (or even transparent) appearance. Further disclosed is a method of preparation of such composition, as well as a method of its use.

20 Claims, No Drawings

TRANSLUCENT AND SYRUPY COSMETIC COMPOSITION

FIELD OF THE INVENTION

The present invention relates to a stable cosmetic composition having a syrupy texture while not being sticky, and translucent (or even transparent) appearance.

BACKGROUND OF THE INVENTION

The stability is one of the most essential factors for a cosmetic composition, since it allows assuring a good quality of a cosmetic product for customers.

Viscosity of a cosmetic composition is also an important factor, not only from the point of view of customer satisfaction, but also from the technical point of view.

Indeed, customers appreciate a rich hand feeling, that is to say, a sufficient consistency.

At the same time, a cosmetic composition packaged in a container must be easily taken out at the time of use.

There exist today various types of containers for cosmetic compositions.

A pipettable bottle is one of the most frequently used forms of containers for cosmetic compositions. It is particularly convenient in the cosmetic field, notably for cosmetic products applied in a small quantity.

In order to be pipettable, the cosmetic composition must have a specific viscosity. Indeed, a particular rheological property is required so that the composition can be pipettable.

Therefore the composition must be fluid enough to be pipetted from the container to the outside, and must be hard enough to have consistency in the hand.

Furthermore, translucency is often sought by the manufacturers of cosmetic products, particularly because it gives them more freedom of formulation of a variety of final products.

Researches have been carried out to propose such a cosmetic composition.

The patent FR 03 12595 discloses a transparent or clear emulsion for cosmetic or pharmaceutical use, comprising a fatty phase comprising at least a lipophilic solvent, an aqueous phase, and an emulsifying system comprising at least an ester of non-ethoxylated fatty acid having a HLB comprised between 11 and 16.

The patent application EP 2 218 439 relates to a cosmetic composition for make-up removal, comprising an aqueous phase, at least 35 weight % of jojoba oil with respect to the total weight of the composition, and at least an ester of sucrose and fatty acid.

The patent application EP 2 218 440 discloses a cosmetic composition for make-up removal, comprising an aqueous phase, a lipophilic compound, and an emulsifying system comprising a sucrose ester and an ester of polyglycerol and of fatty acid.

Also, there already exist on the market products to be pipetted in the form of water-in-silicon emulsion or aqueous gel.

The water-in-silicon emulsion is not appreciated by customers because of its silicon touch. The aqueous gel lacks comfortable touch and does not give a sensation of richness.

None of these documents or products discloses a stable cosmetic composition having a translucency, and an appropriate viscosity for pipettable bottle.

Thus there is still a need for a stable cosmetic composition having a syrupy texture while not being sticky, and translucent (or even transparent) appearance.

The applicant has found out that these technical problems are solved by the cosmetic composition of the present invention.

SUMMARY OF THE INVENTION

According to a first aspect, the present invention relates to a cosmetic composition in the form of an oil-in-water emulsion comprising, in a physiologically acceptable medium:
(A) an emulsifying system comprising sucrose palmitate and/or sucrose laurate,
(B) an aqueous phase comprising water and glycerol in a weight ratio water/glycerol ranging from 0.1/1 to 1/1, and preferably from 0.2/1 to 0.6/1, and
(C) at least 50% by weight, preferably at least 55%, and more preferably 57% by weight with respect to the total weight of the composition, of fatty phase, comprising one or more oily esters of $C_6$-$C_{12}$ fatty acids and of $C_6$-$C_{18}$ fatty mono-alcohols.

According to a second aspect, the present invention relates to a method of preparing the cosmetic composition described above, comprising the steps of
1—slowly adding the fatty phase (C) to the aqueous phase (B), under stirring,
2—gradually increasing the stirring speed so as to obtain an emulsion, and
3—letting the obtained emulsion get cool.

According to a third aspect, the present invention relates to a use of the cosmetic composition described above, for skin care.

DETAILED DESCRIPTION OF THE INVENTION

The Cosmetic Composition

The composition of the invention is intended to be applied on the facial skin and/or neck skin in the form of a "serum" concentrated in active agents, in order to prevent or reduce the cutaneous signs of aging. It can be applied either as a cream or a care fluid, or as a mixture of both. Generally, this composition is sufficiently fluid so that one can apply only one drop of this composition onto the skin, and then spread it by his finger across the entire face. Its texture is syrupy enough to be felt as rich when the composition is pipetted from its container, but without generating any sticky sensation on the skin.

The composition of the invention is also stable. By "stable", it is meant that after 3 months of storage at room temperature, at 40° C. and at 45° C. the composition does not show any physical change visible to the naked eye, such as a phenomenon of creaming or phase separation or alteration of its color.

The composition of the present invention is in the form of an oil-in-water emulsion comprising, in a physiologically acceptable medium:
(A) an emulsifying system comprising sucrose palmitate and/or sucrose laurate,
(B) an aqueous phase comprising water and glycerol in a weight ratio water/glycerol ranging from 0.1/1 to 1/1, and preferably from 0.2/1 to 0.6/1, and
(C) at least 50% by weight, preferably at least 55%, and more preferably 57% by weight with respect to the total weight of the composition, of fatty phase, comprising one or more oily esters of $C_6$-$C_{12}$ fatty acids and of $C_6$-$C_{18}$ fatty mono-alcohols.

As used herein, "sucrose palmitate" (CAS N° 26446-38-8) and "sucrose laurate" (CAS N° 25339-99-5) are esters of sucrose and fatty acids, respectively lauric acid and palmitic acid.

They are commercially available, for example, from Gattefosse under the trade name of Surhope C1216® (sucrose laurate) and Sucrose C1616® (sucrose palmitate) respectively.

Without wishing to be bound by theory, these sucroesters form a lamellar structure system, which allows obtaining the appropriate viscosity according to the present invention.

Emulsifying System

The composition of the present invention comprises an emulsifying system comprising sucrose palmitate and/or sucrose laurate.

In addition, each of the sucrose palmitate and sucrose laurate is advantageously present in said emulsifying system in an amount of from 1 to 3% by weight, preferably from 1 to 2% by weight, and more preferably 1.5% by weight, with respect to the total weight of the composition.

In a particularly advantageous embodiment of the present invention, said emulsifying system (A) comprises a mixture of sucrose laurate and sucrose palmitate at a weight ratio of 1:1.

It is preferred that the emulsifying system comprises from 0 to 1% by weight, with respect to the total weight of the composition, of surfactants other than sucrose laurate and sucrose palmitate.

In addition to the emulsifying system cited above, the composition of the invention comprises an aqueous phase and a fatty phase.

Aqueous Phase

According to the Present Invention, the Ratio between glycerol and water ranges from 0.1/1 to 1/1, and preferably from 0.2/1 to 0.6/1.

Without wishing to be bound by theory, the Applicant has discovered that the above mentioned ratio of glycerol/water allows conferring to the cosmetic composition the required translucency and viscosity.

The aqueous phase comprises water and glycerol in a given weight ratio, and which together represent 25 to 35% by weight, with respect to the total weight of the composition, according to a preferred embodiment. It is also preferred that the aqueous phase comprises no hydrophilic gelling agent.

Fatty Phase

The fatty phase is present in the cosmetic composition, at a level of at least 50%, preferably at least 55%, and more preferably at least 57% by weight with respect to the total weight of the composition, comprising one or more oily esters of $C_6$-$C_{12}$ fatty acids and of $C_6$-$C_{18}$ fatty mono-alcohols.

As used herein, "oily esters of $C_6$-$C_{12}$ fatty acids and $C_6$-$C_{18}$ fatty mono-alcohols" are esters of fatty acids having 6 to 12 carbon atoms, with fatty mono-alcohols having 6 to 18 carbon atoms.

Said oily esters are obtained from $C_6$-$C_{12}$ fatty acids, preferably $C_8$-$C_{10}$ fatty acids, and from $C_6$-$C_{18}$ fatty mono-alcohols, preferably $C_8$-$C_{18}$ fatty mono-alcohols.

Examples of "oily esters of fatty acids of $C_6$-$C_{12}$ and fatty mono-alcohols of $C_6$-$C_{18}$" are isononyl isononanoate or coco caprylate. Isononyl isononanoate is commercially available, for example, from Alzo, under the trade name of Wickenol 151.

The oily esters according to the present invention can be, in particular, selected from coco caprylate and isononyl isononanoate. In a particularly preferred embodiment, said oily esters are coco caprylate.

Without wishing to be bound by theory, the Applicant found out that coco caprylate is more stable than other esters, and provides a good feeling to the composition; its residual touch is very light, and has a low density, thus it is more appropriate for the present cosmetic formulation.

Preferably, the coco caprylate is commercialized under the trade mark Cetiol C5 from COGNIS/BASF.

In addition to the oily esters, the fatty phase may comprise volatile hydrocarbon oils, such as isododecane, isohexadecane or vegetable oils, particularly jojoba oils and camellia oils.

It particularly comprises oily esters at a level of from 45 to 90% by weight, preferably from 50 to 85% by weight, with respect to the weight of the fatty phase.

Viscosity

According to a preferred embodiment, the cosmetic composition of the present invention has a viscosity without shear of less than 2300 Pa·s, preferably comprised between 950 and 1800 Pa·s, and more preferably comprised between 980 and 1150 Pa·s, and a threshold stress of less than 10 Pa. Preferably, the threshold stress of the composition is less than 2 Pa.

Preferably, the composition has a viscosity at 100 $s^{-1}$ comprised between 1 and 3 Pa·s.

Active Agents(s)

The composition may also comprise cosmetic active ingredients such as Vanilla planifolia PFA, Vanilla Flower Extract, konjac extract (Konjirides), acylated oligopeptides (such as Matrixyl 3000® of SEDERMA), Vanilla butter and Planifolia Intense Water.

The Vanilla Planifolia PFA can be present advantageously in a weight amount of, for example, 0.20% by weight, with respect to the total weight of the composition.

Vanilla Flower Extract can be present advantageously in a weight amount of, for example 0.11% by weight, with respect to the total weight of the composition.

Konjirides can be present advantageously in a weight amount of, for example 4% by weight, with respect to the total weight of the composition.

Matrixyl 3000® can be present advantageously in a weight amount of, for example 3% by weight, with respect to the total weight of the composition.

Vanilla butter can be present advantageously in a weight amount of, for example 0.5% by weight, with respect to the total weight of the composition.

Planifolia Intense Water can be present advantageously in a weight amount of, for example 0.43% by weight, with respect to the total weight of the composition.

Furthermore, the composition according to the present invention may possibly comprise various active agents selected from vitamins, antioxidants, hydrating agents, anti-pollution agents, keratolytic agents, anti-inflammatory agents, astringents, whitening agents and agents that promote microcirculation.

Examples of vitamins include vitamins A, B1, B2, B6, C and E and their derivatives, pantothenic acid and its derivatives and biotin.

Examples of antioxidants include ascorbic acid and its derivatives such as ascorbyl palmitate, ascorbyl tetraisopalmitate, ascorbyl glucoside, magnesium ascorbyl phosphate, sodium ascorbyl phosphate and ascorbyl sorbate; tocopherol and its derivatives, such as tocopheryl acetate, tocopheryl sorbate, and other esters of tocopherol; dibutyl hydroxytoluene (BHT) and butylated hydroxyanisole (BHA); gallic acid ester; phosphoric acid; citric acid; maleic acid; malonic acid; succinic acid; fumaric acid; cephalin; a hexametaphosphate; phytic acid; ethylenediaminetetraacetic acid; and plant extracts, for instance from *Chondrus cripsus, Rhodiola, Thermus thermophilus*, mate leaf, oak wood, kayu rapet bark, sakura leaves and ylang ylang leaves.

Examples of hydrating agents include polyethylene glycol, propylene glycol, dipropylene glycol, glycerol, butylene glycol, xylitol, sorbitol, maltitol, mucopolysaccharides, such as chondroitin sulfuric acid, hyaluronic acid of high or low molecular weight or hyaluronic acid potentiated by a silanol derivative such as the active Epidermosil® commercialized by the company Exsymol; caronic acid; biliary salts, a salt of pyrrolidone carboxylic acid and a salt of lactic acid, an amino acid analog such as urea, cysteine and serine; short chain soluble collagen, the PPG diglycerol, homo- and copolymers of 2-methacryloyloxyethylphosphorylcholine such as Lipidure HM and Lipidure PBM of NOF; allantoin, glycerol derivatives such as PEG/PPG/polybutylene Glycol-8/5/3 Glycerol of NOF sold under the trade name of Wilbride®S753 or glyceryl-polymethyl of Sederma sold under the trade name Lubragel® MS; trimethylglycine sold under the trade name Aminocoat® by the company Ashahi Kasei Chemicals and various plant extracts such as extracts of *Castanea sativa*, of hydrolysed hazelnut protein, *Tuberosa polyanthes* polysaccharides, kernel oil of *Argania spinosa* and extracts of nacre comprising conchiolin which are sold notably by the company Maruzen (Japan) under the trade name Pearl Extract®.

Other examples of hydrating agents include compounds stimulating the expression of matriptase MT/SP1, such as an extract of carob pulp, as well as agents that stimulate the expression of FN3K; agents which enhance the proliferation or differentiation of keratinocytes such as extracts of *Thermus thermophilus* or of *Camellia Japonica* Alba Plena flower or husks of *Theobroma cacao* beans, the water-soluble extracts of maize, the peptide extracts of *Voandzeia subterranea* and niacinamide, the epidermal lipids and agents that increase the synthesis of epidermal lipids, such as ceramides, phospholipids, and lupine protein hydrolysates.

Examples of anti-pollution agents include the *Moringa pterygosperma* seed extract (for example Purisoft® of LSN), shear butter extract (for example Detoxyl® of Silab), a mixture of extract of ivy and phytic acid, sunflower seed extract (for example Osmopur® of Sederma).

Examples of keratolytic agents include α-hydroxy acids (for example glycolic, lactic, citric, malic, mandelic, or tartaric acid) and β-hydroxy acids (eg salicylic acid), and their esters, such as C12-13 alkyl lactate, and plant extracts comprising these hydroxy acids, such as extracts of *Hibiscus sabdriffa*.

Examples of anti-inflammatory agents include bisabolol, allantoin, tranexamic acid, zinc oxide, sulfur oxide and its derivatives, chondroitin sulfate, glycyrrhizinic acid and its derivatives such as the glycyrrhizinates.

Examples of astringent extracts include witch hazel.

Examples of bleaching agents include arbutin and its derivatives, ferulic acid (such as Cytovector®: water, glycol, lecithin, ferulic acid, hydroxyethyl cellulose commercialized by BASF) and its derivatives, kojic acid, the resorcinol, ellagic acid, leucodopachrome and its derivatives, vitamin B3, linoleic acid and its derivatives, ceramides and their counterparts, a peptide as described in the patent application WO2009010356, a prodrug as described in the patent application WO2006134282 or a salt of tranexamate such as the hydrochloride salt of cetyl tranexamate, an extract of licorice (*Glycyrrhiza glabra* extract), which is notably sold by the company Maruzen under the trade name Licorice Extract®, a bleaching agent having also an antioxidant effect such as vitamin C compounds, including ascorbate salts, ascorbyl esters of fatty acids or of sorbic acid, and other derivatives of ascorbic acid, for example, magnesium ascorbyl phosphate and sodium ascorbyl phosphate, or saccharide esters of ascorbic acid, which include, for example, ascorbyl-2-glucoside, L-ascorbate 2-O-alpha-D-glucopyranosyl, or L-ascorbate 6-O-beta-D-galactopyranosyl. An active agent of this type is sold in particular by the company DKSH under the trade name Ascorbyl Glucoside®.

Examples of agents that promote microcirculation include extract of lupine (such as Eclaline® from Silab), of ruscus, of *Aesculus*, of ivy, of ginseng or of sweet clover extract, caffeine, nicotinate and its derivatives, an algae extract from *Corallina officinalis* such as that commercialized by CODIF; and mixtures thereof. These active agents on the cutaneous microcirculation can be used to avoid tarnishing of the complexion and/or improve the homogenisation and the radiance of the complexion.

Additive(s)

The composition according to the present invention may possibly comprise various additives which can be selected from preservatives, UV filters, perfumes, and mixtures thereof.

Examples of preservatives are benzoic acid, propionic acid, salicylic acid, sorbic acid, biphenyl-2ol (o-phenylphenol), 4-hydroxybenzoic acid, chlorobutanol, 3-acetyl-6-methylpyran-2,4(3H)-dione (dehydroacetic acid), formic acid, 3,3'-dibromo-4,4'-hexamethylene-dioxydibenzamidine (Dibromohexamidine), undec-10-enoic acid and the salts thereof, formaldehyde, paraformaldehyde, pentylene glycol, caprylyl glycol phenoxyethanol and zinc pyrithione.

Examples of UV filter(s) are organic filters, such as the dibenzoylmethane derivatives (including butyl methoxydibenzoylmethane sold in particular by DSM under the trade name Parsol® 1789), the derivatives of cinnamic acid (including ethylhexyl methoxycinnamate sold in particular by DSM under the trade name Parsol® MCX), the salicylates, the para-aminobenzoic acid, the β-β'-diphenylacrylates, benzophenones, the derivatives of benzylidene camphor, the phenylbenzimidazoles, the triazines, the phenylbenzotriazoles and the anthranilic derivatives; or the inorganic filters, based on inorganic oxides in the form of pigments or of nanopigments, coated or not, and in particular based on titanium dioxide or zinc oxide; preferably in an amount from 0.1 to about 30%, better, from 0.5 to 20% by weight, with respect to the total weight of the composition.

This composition has a pH generally comprised between 5 and 6, preferably between 5 and 5.5, with the boundary values included.

Preparation of the Composition Preparation of the Composition

The composition according to the present invention can be prepared by any method known to a person skilled in the art.

The composition according to the invention can preferably be prepared by a method comprising the successive steps of:

1—slowly adding the fatty phase (C) to the aqueous phase (B), under stirring,

2—gradually increasing the stirring speed so as to obtain an emulsion, and

3—letting the obtained emulsion get cool.

In case of "a cold process", the components of aqueous phase and of fatty phase are kept at ambient temperature, that is to say, about 20-25° C.

In case of "a hot process", the following step is carried out before the step 1 of the above mentioned method:

separately heating the aqueous phase (B) and the fatty phase (C) at a temperature of 70 to 75° C.

The Applicant has discovered that a hot process allows obtaining a thicker and more transparent composition.

Furthermore, the applicant has also discovered that a hot process allows providing a composition as stable as a composition prepared in a cold process, but with 50% less amount of sucroesters.

This is thus economically interesting for the present invention.

Use

The composition of the present invention can be used for skin care, particularly for preventing skin ageing, preferably of neck and face skin.

Said composition can be applied on face and/or neck skin, before application of a cream or as a mixture with the cream.

The invention will be illustrated by the non-limiting following examples.

Example 1: A Cosmetic Composition

The following composition was prepared. The proportions of ingredients are weight percentages with respect to the total weight of the composition:

| (A) Emulsifying system | |
|---|---|
| Sucrose palmitate | 1.5% |
| Sucrose laurate | 1.5% |
| (B) Aqueous Phase | |
| Water | 5-10% |
| Glycerol | 20-30% |
| Caprylyl glycol | 0.1-1% |
| Antioxidant | 0.1-1% |
| (C) Fatty phase | |
| Vegetable oils | 5-10% |
| Isononyl isononanoate | 25-35% |
| Isohexadecane | 15-25% | provided that the total of these constituents is equal to 100%.

Example 2: A Cosmetic Composition

The following composition was prepared. The proportions of ingredients are weight percentages with respect to the total weight of the composition:

| (A) Emulsifying system | |
|---|---|
| Sucrose palmitate | 1.5% |
| Sucroselaurate | 1.5% |
| (B) Aqueous Phase | |
| Water | 5-10% |
| Glycerol | 20-30% |
| Caprylyl glycol | 0.1-1% |
| Antioxidant | 0.1-1% |
| (C) Fatty phase | |
| Vegetable oils | 5-10% |
| coco caprylate | 45-55% | provided that the total of these constituents is equal to 100%.

Example 3: Rheological Study

The compositions in Table 1 have been prepared.

The viscosity without shear, threshold stress and viscosity at 100 $s^{-1}$ have been measured at 20° C. with a Rheometer Gémini (Malvern Instruments).

It should be noted that they all have a viscosity without shear less than 2200 Pa·s and threshold stress less than 10 Pa.

They are stable, as shown in Table 1.

The first trial (Ref. 1) was performed with a mixture of sucrose myristate and sucrose stearate, each comprised at a level of 3%. However, this couple of sucroesters does not form a stable emulsion and presents a phenomenon of creaming.

Consequently, other sucroesters were tested: sucrose laurate and sucrose palmitate, each comprised at a level of 3% (Ref. 2). The emulsion stability is correct, however the product is too thick and it was not translucent.

The concentration of sucrose esters was then reduced to 2% each (Ex 1) to further decrease the viscosity, and the concentration of glycerol was increased to obtain a transparent emulsion. The emulsion was thick and stable.

The concentration of surcoesters was again reduced to 1.5% each (Ex 2) to obtain the desired viscosity. The resulting emulsion is translucent and "syrupy" and stable.

However, the residual touch is a little too fat. Therefore, each ingredient of the oil phase was decreased by 10% (Ref. 3): the emulsion is stable, but is not translucent, and the cosmeticity of the emulsion remained too fat.

Another approach to decrease the "fat" sensation was to remove the butter (Butyrospermum Parkii; phytosteryl Canola Glycerides and Vanilla Butter) of the formula (Ex. 3). The ratio of glycerol/water was also changed to keep the translucency of the emulsion. The viscosity and translucency of the products are optimal and the emulsion is stable.

To ensure an antimicrobial preservative, phenoxyethanol 0.5% was added (Ex. 4). As in previous tests, the ratio of glycerol/water was also changed to keep the translucency of the emulsion. The viscosity of the product is correct, and the emulsion is stable.

The coco-caprylate is a naturally occurring ester having a light and non greasy touch. Another line of naturally occurring oil was tested (Ref. 4) with sunflower oil (*Helianthus annuus* seed oil). The emulsion has an acceptable viscosity; however, it is opaque and has a residual touch much richer than Ex. 4.

TABLE 1

Cosmetic compositions and their viscosities

| | | Ref. 1 | Ref. 2 | Ex. 1 | Ex. 2 | Ref. 3 | Ex. 3 | Ex. 4 | Ref. 4 |
|---|---|---|---|---|---|---|---|---|---|
| Sucrose esters | SUCROSE LAURATE (C12) | — | 3 | 2 | 1.5 | 1.5 | 1.5 | 1.5 | 1.5 |

TABLE 1-continued

Cosmetic compositions and their viscosities

|  |  | Ref. 1 | Ref. 2 | Ex. 1 | Ex. 2 | Ref. 3 | Ex. 3 | Ex. 4 | Ref. 4 |
|---|---|---|---|---|---|---|---|---|---|
|  | SUCROSE PALMITATE (C16) | — | 3 | 2 | 1.5 | 1.5 | 1.5 | 1.5 | 1.5 |
|  | SUCROSE MYRISTATE (C14) | 3 | — | — | — | — | — | — | — |
|  | SUCROSE STEARATE (C18) | 3 | — | — | — | — | — | — | — |
| Aqueous phase | GLYCEROL | 20 | 10 | 21 | 23.64 | 26.483 | 23.64 | 23.13 | 23.13 |
|  | WATER | 6 | 16 | 7 | qs | qs | qs | qs | qs |
|  | *VANILLA PLANIFOLIA* FRUIT WATER | 4 | 4 | 4 | 0.2 | — | — | — | — |
|  | CAPRYLYL GLYCOL | 0.25 | 0.25 | 0.25 | 0.25 | 0.25 | 0.25 | 0.25 | 0.25 |
|  | Solid citric acid (50%) | — | — | — | 0.018 | 0.018 | 0.01 | 0.01 | 0.01 |
|  | PHENOXYETHANOL | — | — | — | — | — | — | 0.5 | 0.5 |
| Fatty phase | *SIMMONDSIA CHINENSIS* (JOJOBA) SEED OIL | 5 | 5 | 5 | 5 | 4.5 | 5 | 5 | 5 |
|  | *CAMELLIA KISSI* SEED OIL | 2 | 2 | 2 | 2 | 1.8 | 2 | 2 | 2 |
|  | BUTYROSPERMUM PARKII (Lipex SHEA U) | 2.5 | 2.5 | 2.5 | 2.5 | 2.25 | — | — | — |
|  | PHYTOSTERYL CANOLA GLYCERIDES (Lipex Cellect) | 2.5 | 2.5 | 2.5 | 2.5 | 2.25 | — | — | — |
|  | HYDROGENATED VEGETABLE OIL (Akorex L) | 2 | 2 | 2 | 2 | 1.8 | 2 | 2 | 2 |
|  | MINERAL OIL | — | — | — | — | — | — | — | — |
|  | CAPRYLIC/CAPRIC TRIGLYCERIDE | — | — | — | — | — | — | — | — |
|  | Vanilla butter | — | — | — | 0.5 | 0.45 | — | — | — |
|  | COCO-CAPRYLATE (Cetiol C5) | 49.15 | 49.15 | 49.15 | 45.35 | 40.81 | 50.35 | 50.35 | — |
|  | DICAPRYLYL CARBONATE | — | — | — | — | — | — | — | — |
|  | *HELIANTHUS ANNUUS* (SUNFLOWER) SEED OIL (AKOSUN) | — | — | — | — | — | — | — | 50.35 |
| ACTIFS | *VANILLA PLANIFOLIA* FRUIT OIL | 0.1 | 0.1 | 0.1 | — | — | — | — | — |
|  | *VANILLA PLANIFOLIA* PFA | — | — | — | 0.2 | 0.2 | 0.2 | 0.2 | 0.2 |
|  | TOCOPHERYL ACETATE | 0.5 | 0.5 | 0.5 | 0.5 | 0.5 | 0.5 | 0.5 | 0.5 |
|  | *PLANIFOLIA* INTENSE WATER | — | — | — | 0.474 | 0.6 | 0.474 | 0.43 | 0.43 |
|  | *VANILLA* FLOWER EXTRACT | — | — | — | 0.11 | 0.11 | 0.11 | 0.11 | 0.11 |
|  | KONJIRIDES | — | — | — | 4 | 4 | 4 | 4 | 4 |
|  | MATRIXYL 3000 | — | — | — | 3 | 3 | 3 | 3 | 3 |
| Coloring agent | TINCTAMI GARANCE | — | — | — | — | 0.4 | 0.48 | 0.48 | 0.48 |
| Solution of sodium hydroxyde (25%) |  | — | — | — | — | — | 0.01 | 0.01 | 0.01 |
| Aspect |  | Opalescent Translucid | opaque | translucid | translucid | opaque | transparent | translucid | opaque |
| Physical stability TA 3M |  | crémage | RAS | RAS | RAS | RAS | RAS | RAS | RAS |
| Thermic stabilities 40° C. and 45° C. at 3M |  | crémage | RAS | RAS | RAS | RAS | RAS | RAS | RAS |
| Viscosity LVT needle S63; 3 rpm (cp) |  | — | — | — | 1500 | 4000 | 1400 | 22000 | 3400 |
| Time interval |  | — | J + 1 year | J + 1 year | — | J + 9 months | J + 7 months | — | J + 7 days |
| Viscosity without shear (Pa · s) |  | — | 885 ± 55 | 2116 ± 119 | — | 84 ± 7 | 1054 ± 69 | 1639 ± 145 | 3028 ± 118 |
| Threshold stress (Pa) |  | — | 0.6 ± 0.1 | 1.3 ± 0.1 | — | 0.15 ± 0.02 | 0.58 ± 0.02 | 0.98 ± 0.05 | 1.7 ± 0.1 |
| Viscosity at 100 s$^{-1}$ (Pa · s) |  | — | 0.44 ± 0.01 | 1.23 ± 0.05 | — | 2.43 ± 0.02 | 1.19 ± 0.01 | 1.297 ± 0.02 | 1.297 ± 0.02 |
| pH |  | — | — | — | 4.9 | 5 | 5.4 | 5.2 | 5.7 |

The invention claimed is:

1. A cosmetic composition in the form of an oil-in-water emulsion comprising, in a physiologically acceptable medium:
   (A) an emulsifying system consisting of sucrose palmitate and sucrose laurate, wherein each of the sucrose palmitate and the sucrose laurate is present in said emulsifying system (A) in a weight amount of from 1 to 2% by weight with respect to the total weight of the composition,
   (B) an aqueous phase comprising water and glycerol in a weight ratio water/glycerol ranging from 0.1/1 to 1/1, said water and said glycerol in said aqueous phase together represent 25 to 35% by weight of the total weight of the composition, (C) at least 57% by weight with respect to the total weight of the composition, of fatty phase, comprising one or more oils selected from group consisting of a vegetable oil, isododecane, and isohexadecane, and one or more oily esters of fatty acids, wherein said oily esters are present at a level of from 50 to 90% by weight, with respect to the weight of said fatty phase, wherein said oily esters are selected from isononyl isononanoate and coco caprylate, wherein the composition is translucent or transparent.

2. The cosmetic composition according to claim 1, wherein said cosmetic composition has a viscosity without shear of less than 2300 Pa·s and a threshold stress of less than 10 Pa, the viscosity without shear, threshold stress and viscosity at $100s^{-1}$ being measured at 20° C. with a Rheometer Gemini from Malvern Instruments.

3. The cosmetic composition according to claim 1, wherein said emulsifying system (A) consists of a mixture of sucrose laurate and sucrose palmitate at a weight ratio of 1:1.

4. The cosmetic composition according to claim 1, wherein said oily esters are coco caprylate.

5. The cosmetic composition according to claim 1, wherein said fatty phase (C) comprises one or more vegetable oils selected from the group consisting of jojoba oils and camellia oils and combinations thereof.

6. The cosmetic composition according to claim 1, wherein said cosmetic composition further comprises at least an active ingredient selected from Vanilla Planifolia PFA, Vanilla Flower Extract, konjac extract, acylated oligopeptides, Vanilla butter and Planifolia Intense Water.

7. The cosmetic composition according to claim 1, wherein said cosmetic composition further comprises at least an additive selected from preservatives, UV filters, perfumes and mixtures thereof.

8. A method of preparing the cosmetic composition according to claim 1, comprising the successive steps of:
(i) providing the aqueous phase (B) and the fatty phase (C) separately;
(ii) under stirring at a speed slowly adding the fatty phase (C) in an amount that is at least 57% by weight with respect to the total weight of the composition to the aqueous phase (B), the fatty phase (C) comprising one or more oils selected from a vegetable oil, isododecane, isohexadecane, and one or more oily esters of fatty acids, wherein said oily esters are present at a level of from 50 to 90% by weight with respect to the weight of said fatty phase, wherein said oily esters are selected from isononyl isononanoate and coco caprylate, the aqueous phase (B) comprising water and glycerol in a weight ratio water/glycerol ranging from 0.1/1 to 1/1, said water and said glycerol in said aqueous phase together represent 25 to 35% by weight of the total weight of the composition, said aqueous phase further comprising an emulsifying system consisting of sucrose palmitate and sucrose laurate, wherein each of the sucrose palmitate and the sucrose laurate is present in said emulsifying system (A) in a weight amount of from 1 to 2% by weight with respect to the total weight of the composition,
(iii) optionally a heating step,
(iv) gradually increasing the stirring speed so as to obtain an emulsion, and
(v) cooling the obtained emulsion to the ambient temperature.

9. The method according to claim 8, wherein the heating step is carried out before the step (ii); and said heating step comprising separately heating the aqueous phase (C) and the fatty phase (B) at 70 to 75° C.

10. A method for reducing cutaneous sings of aging, comprising applying an effective amount of the composition according to claim 1.

11. The cosmetic composition according to claim 2, wherein said emulsifying system (A) consists a mixture of sucrose laurate and sucrose palmitate at a weight ratio of 1:1.

12. The cosmetic composition according to claim 1, wherein said emulsifying system (A) consists a mixture of sucrose laurate and sucrose palmitate at a weight ratio of 1:1.

13. The cosmetic composition according to claim 1, wherein the aqueous phase (B) comprises water and glycerol in a weight ratio water/glycerol ranging from 0.2/1 to 0.6/1.

14. The cosmetic composition according to claim 2, wherein said cosmetic composition has a viscosity without shear of between 950 and 1800 Pa·s., the viscosity without shear, threshold stress and viscosity at $100 \text{ s}^{-1}$ being measured at 20° C. with a Rheometer Gémini from Malvern Instruments.

15. The cosmetic composition according to claim 14, wherein said cosmetic composition has a viscosity without shear of between 980 and 1150 Pa·s, the viscosity without shear, threshold stress and viscosity at $100 \text{ s}^{-1}$ being measured at 20° C. with a Rheometer Gemini from Malvern Instruments.

16. The cosmetic composition according to claim 1, wherein each of sucrose palmitate and sucrose laurate is present in said emulsifying system (A) in a weight amount of 1.5% with respect to the total weight of the composition.

17. The cosmetic composition according to claim 1, wherein the fatty phase comprises isohexadecane and isononyl isononanoate, said isohexadecane being present in an amount that is 15 to 25% by weight of the total composition and said isononyl isononanoate being present in an amount that is 25 to 35% by weight of the total composition.

18. The cosmetic composition according to claim 17, wherein the fatty phase further comprises one or more vegetable oils, said one or more vegetable oils being present in an amount that is 5 to 10% by weight of the total composition.

19. The cosmetic composition according to claim 1, wherein the fatty phase comprises coco caprylate and one or more vegetable oils, said coco caprylate being present in an amount that is 45 to 55% by weight of the total composition and said one or more vegetable oils being in an amount that is 5 to 10% by weight of the total composition.

20. A cosmetic composition in the form of an oil-in-water emulsion comprising, in a physiologically acceptable medium:

(A) an emulsifying system consisting of sucrose palmitate and sucrose laurate, wherein each of the sucrose palmitate and the sucrose laurate is present in said emulsifying system (A) in a weight amount of from 1 to 2% by weight with respect to the total weight of the composition, (B) an aqueous phase comprising water and glycerol in a weight ratio water/glycerol ranging from 0.1/1 to 1/1, said water and said glycerol being 25% to 35% by weight with respect to the total weight of the composition, (C) a fatty phase that is at least 57% by weight with respect to the total weight of the composition, the fatty phase comprises one or more oily esters and one or more oils, the one or more oily esters being selected from the group consisting of iosnyl isononanoate and coco caprylate, the one or more oily esters being present in an amount of 50% to 90% by weight of the fatty phase, the one or more oils being selected from the group consisting of (i) one or more vegetable oils present in an amount that is 5 to 10% by weight of the total composition, (ii) isohexadecane present in an amount that is 15 to 25% by weight of the total composition, and (iii) combinations thereof, and (D) a cosmetic active agent selected from the group consisting of from Vanilla Planifolia PFA, Vanilla Flower Extract, konjac extract, acylated oligopeptides, Vanilla butter, Planifolia Intense Water and combinations thereof, wherein the composition is translucent or transparent.

* * * * *